United States Patent [19]

Peyman et al.

[11] Patent Number: 5,219,844
[45] Date of Patent: Jun. 15, 1993

[54] COMBINATION OF PERFLUOROCARBON LIQUID AND SILICONE AND METHOD OF TREATING DISORDERS OF AN EYE WITH THE COMBINATION

[76] Inventors: Gholam A. Peyman, 2020 Gravier St., Suite B, New Orleans, La. 70112-2234; Leland C. Clark, Jr., Ellard and Bethesda Ave., Cincinnati, Ohio 45229

[21] Appl. No.: 861,178

[22] Filed: Mar. 27, 1992

Related U.S. Application Data

[63] Continuation of Ser. No. 636,664, Jan. 2, 1991, abandoned.

[51] Int. Cl.$^5$ ............... A61K 31/695; A61K 47/00
[52] U.S. Cl. ........................ 514/63; 514/772
[58] Field of Search ............. 514/63, 772, 832

[56] References Cited

PUBLICATIONS

Toxiline, 02439932 (1989). Liu et al.
Toxiline, 02352234 (1989). Nabih et al.
Experimental Evaluation of Low-Viscosity Fluorosilicone Oil as a Temporary Vitreous Substitue—K-wan-Rong Liu, MD, Gholam A. Paymen, MD Michael V. Miceli, PhD Oct. (1989).
Experimental Evaluation of Perfluorophenanthrene as a High Specific Gravity Vitreous Substitute: Apr. (1989). A Preliminary Report—Mostafa Nabih, MD, Gholam A. Peyman, MD, Leland C. Clark, Jr., PhD, Righard E. Hoffman, PhD, Michael Miceli, PhD, Mahmoud Abou-Steit, MD, Magdy Tawakol, MD, Kwan-Rong Liu, MD.

*Primary Examiner*—Frederick E. Waddell
*Assistant Examiner*—Zohreh A. Fay
*Attorney, Agent, or Firm*—Haverstock, Garrett & Roberts

[57] ABSTRACT

A combination of perfluorocarbon liquid and silicone is used to treat ophthalmological disorders of the eye. Perfluorocarbon liquid and silicone are injected into the eye to treat detached or torn retinas. A method of treating ophthalmological disorder of the eye with the combination of perfluorocarbon liquid and silicone is also disclosed.

20 Claims, No Drawings ered and perfluorocarbons
COMBINATION OF PERFLUOROCARBON LIQUID AND SILICONE AND METHOD OF TREATING DISORDERS OF AN EYE WITH THE COMBINATION This is a continuation of copending application Ser. No. 07/636,664 filed on Jan. 2, 1991, now abandoned.

BACKGROUND OF THE INVENTION

The present invention relates to a combination of perfluorocarbon liquid and silicone for treating disorders of an eye and more particularly to a combination of perfluorophenanthrene and silicone as an interoperative tool and methods of treating disorders of an eye with the combination.

Retinal detachment consists of physical separation of the retina from its juxtaposition to the choroid. One of the most important factors contributing to retinal detachment is liquefaction and shrinkage of the vitreous, commonly referred to as vitreous retraction. Additionally, vitreous retraction caused by vitreous shrinkage may produce retinal tear with or without retinal detachment. For more than three decades lighter-than-water vitreous substitutes, such as silicone and gas, have played an important role in management of complicated retinal detachments, providing short and long term tamponading effect on the retina. Although these substances exert some degree of pressure to the upper part of the retina, the loss of support in the inferior part of the vitreous cavity causes accumulation of fluid with subsequent membrane formation in this area. Thus inferior tractional retinal detachments are often seen with the use of low specific gravity silicone oil. Although high specific gravity fluorosilicone was injected inside the vitreous cavity as early as 1962 by Cibis and others, its effect as a tamponading agent and intraoperative tool was not recognized until years later. The impurities present in fluorosilicone have made it less desirable as a high specific gravity vitreous substitute.

In 1966, Clark, one of the co-inventors herein, reported on the use of fluorocarbon liquids as an oxygen transporter and blood substitute. It has been demonstrated that mice immersed for one hour in a liquid perfluorocarbon equilibrated with oxygen at atmospheric pressure could survive by breathing this oxygenated liquid. In 1982, Haidt et al reported the use of liquid perfluorocarbon as a vitreous substitute. Since then numerous experimental studies have demonstrated poor long term tolerance if these substances are injected in the vitreous cavity. Chang was the first to demonstrate the use of perfluorochemicals as an intraoperative tool in the human eye and recommended their removal immediately during the same procedure.

The common characteristics of perfluorocarbon liquids are their higher specific gravity than that of water, which assists in unfolding the retina, specifically in giant retinal tears. Their low viscosity permits injection through small bore needles, as thin as 20 to 30 gauge, simplifying intravitreal injection and subsequent removal. Their surface tension and immiscibility with water enhances their effect on unfolding the detached retina. Table I demonstrates the majority of presently used perfluorocarbon liquids in ophthalmology and their characteristics.

TABLE I

| Perfluorocarbon Liquids | | | |
|---|---|---|---|
| Perfluorocarbon | Chemical Formula | Specific Gravity | Viscosity (cs, 25 C) |
| Perfluorotributylamine | $C_{12}F_{27}N$ | 1.89 | 2.6 |
| Perfluorooctane | $C_8F_{18}$ | 1.76 | 0.8 |
| Perfluorodecalin | $C_{10}F_{18}$ | 1.94 | 2.7 |
| Vitreon (Perfluorophenanthrene) | $C_{14}F_{24}$ | 2.03 | 8.03 |

| Perfluorocarbon | Refractive Index | Surface Tension dyne/cm |
|---|---|---|
| Perfluortributylamine | 1.29 | 16 |
| Perfluorooctane | 1.27 | 14 |
| Perfluorodecalin | 1.31 | 16 |
| Vitreon (Perfluorophenanthrene) | 1.33 | 16 |

A recurring problem in retinal detachment surgery, especially after the formation of vitreous traction, is maintaining the retina in position until chorioretinal adhesions can form. At present various kinds of gases including air, sulfurhexafluoride, and perfluorocarbons are used to hold the retina in place. However, both giant retinal tears and inferior breaks are difficult to treat with gas.

Experimental studies have demonstrated a new perfluorocarbon liquid (perfluorophenanthrene $C_{12}F_{24}$, also known as Vitreon which is a registered trademark, to have no toxic effect on the tissue culture grown in cells and to be tolerated in vitrectomized rabbit eyes and primate eyes when left for six weeks in the vitreous cavity. However, perfluorophenanthrene, if left in the vitreous cavity too long, fragments into small globules in the vitreous cavity. This phenomenon, referred to as emulsification, has been attributed to the change in the surface tension of substances in the vitreous which are absorbed into the surface of the globule of perfluorophenanthrene. It would be desirable if the lifetime of perfluorocarbon liquids present in the vitreous cavity could be extended up to 2-3 months for use in complex cases of vitreoretinal detachment requiring a long-term tamponading effect. Therefore, there is a need for a vitreous substitute which does not form small globules in the vitreous cavity.

SUMMARY OF THE INVENTION

The combination of perfluorocarbon liquids and silicone has been found to be an acceptable substitute for the vitreous in the vitreous cavity. This combination can be introduced into the vitreous cavity to treat retinal tears or detachments. One beneficial effect of the combination of perfluorocarbon liquids and silicone is that the silicone prevents or hinders the emulsification of perfluorocarbon liquids. This allows the combination to be left in the eye for longer periods of time than previously obtained. Another benefit is that the combination acts like a cast to maintain the retina in position long enough for chorioretinal adhesions to form. The perfluorocarbon liquids provide support of the lower portion of the retina and the silicone provides support of the upper portion of the retina. In the past only support of either the upper or lower portion of the retina was possible, but not simultaneous support of both the upper and lower portions of the retina. Another benefit, which is an unexpected result, is that the combination of perfluorocarbon liquids and silicone is non-toxic.

Accordingly, it is an object of the invention to provide a combination of perfluorocarbon liquid and silicone for a vitreous substitute which prevents emulsification of the perfluorocarbon liquid when left in the vitreous cavity for extended periods of time.

It is a further object of the present invention to use the combination of perfluorocarbon liquid and silicone in a method for treating ophthalmological disorders such as retinal detachments and tears.

These and other objects and advantages of the present invention will become apparent to those skilled in the art after considering the following detailed specification.

DETAILED DESCRIPTION OF PREFERRED EMBODIMENTS

The present invention, in its broadest sense, involves the introduction of the combination of perfluorocarbon liquids and silicone into the eye to treat ophthalmological disorders such as retinal detachments and tears. Prior to the combination of perfluorocarbon liquids and silicone being injected into the eye, the vitreous is removed from the eye. The combination of perfluorocarbon liquids and silicone can be introduced into the eye by different methods of injection. The vitreous of the eye is substantially replaced with the combination of perfluorocarbon liquids and silicone.

The perfluorocarbon may be generally termed as "liquids". The term "liquid", as used herein, is a comprehensive designation incorporating compounds that are in a state neither solid or gaseous such as liquids, emulsions, and gels. The term "perfluorocarbon" means a highly fluorinated compound of carbon. Among the perfluorocarbon liquids which may be employed are perfluorophenanthrene or Vitreon and the other perfluorocarbon liquids listed in Table I. Also, perfluorooctylbromide which is described by its empirical formula of $C_8F_{17}Br$ and its trade name PFOB may also be used. Additionally, the perfluorocarbon compounds disclosed in U.S. Pat. No. 4,490,351 are suitable liquids for use in this invention.

Vitreon is produced up to 99.9999% pure, free of residual components, and sterilized with dry autoclave up to 120° C. for one hour. Vitreon is supplied in single use 10 mL vials from Vitrophage Inc. of Oak Brook, Ill. The injection of Vitreon is performed by using a blunt 20 to 27 gauge needle. Initial experiences with this perfluorocarbon demonstrated that, in the absence of peripheral dialysis or a giant retinal tear, but in the presence of a peripheral retinal tear, it is important to flatten the peripheral part of the retina by performing a limited air-fluid exchange and then filling up the rest of the vitreous cavity with Vitreon and silicone in predetermined amounts. Generally, a posterior retinotomy for the drainage of subretinal fluid is not required. However, a relaxing retinotomy located anterior to the equator or posterior close to the arcade can be performed as needed to relieve severe contraction of the retina. After flattening the retina, argon endolaser photocoagulation (if necessary) is applied over the peripheral and posterior part of the retina in a scatter fashion, excluding the macular area. Prone positioning of a patient is not needed. Patients may sleep in supine positions and sit in chairs during the day with slightly restricted physical activity.

Perfluorocarbon liquids in combination with silicone are an effective intraoperative tamponading tool and long-term postoperative vitreous substitute. In the case of giant retinal tear with rolled over retina and retinal detachment complicated by PVR requiring extensive retinotomy and keratoprosthesis, flattening of the retina could not be achieved with ease and would require intraoperative prone positioning of the patient and the use of intraocular gas or silicone to reattach the retina. Intraoperative use of Vitreon and silicone assists in flattening of the retina in the posterior pole and provides countertraction and stabilization of the retina during the preretinal membrane dissection, especially in the peripheral part of the retina. The use of high specific gravity perfluorocarbon also eliminated the need for drainage of subretinal fluids through posterior retinotomies, thus eliminating potential complications from the site of retinotomies, such as bleeding or membrane formation. The use of perfluorophenanthrene in combination with silicone as a vitreous substitute eliminates the need for prone positioning of patients which otherwise would be required if silicone by itself is used to tamponade the retina.

The invention, its principles and objectives will be further understood in view of the following examples. The following examples illustrate the use of the combination of perfluorocarbon liquids and silicone in the eyes. In the first example, where the ophthalmological disorder is retinal tear in the inferior portion of the eye, a combination of 2 parts perfluorocarbon liquid and 1 part silicone are injected into the eye. In the second example, where the ophthalmological disorder is a retinal tear in the upper portion of the retina, 1 part perfluorocarbon liquid and 2 parts silicone are injected into the eye. Additionally, the combination may include 1 part perfluorocarbon liquid and 1 part silicone injected into the eye. It is to be understood that any proportions of silicone and perfluorocarbon liquid may be used. The decision of what proportion to be used may be made during surgery. It is desirable to inject silicone and perfluorocarbon liquid separately, however, the combination may also be injected simultaneously.

The silicone used in combination with perfluorocarbon liquids is ultra pure. Silicone has a viscosity in the range of 10 centistokes to 12,500 centistokes. However, the preferred range is between 250 centistokes and 1,000 centistokes. It has been determined that the higher the viscosity of the silicone the less likely that the perfluorocarbon liquids will emulsify in the eye. Additionally, fluorosilicone may be used.

The combination of perfluorocarbon liquid and silicone when introduced into the eye has several beneficial effects. One beneficial effect is that the combination of perfluorocarbon liquid and silicone act like a cast to hold the retina in place. Perfluorocarbon liquids have a specific gravity which is heavier than water in the eye and silicone has a specific gravity which is lighter than water in the eye. The perfluorocarbon liquids provide support of the lower portion of the retina and the silicone provides support of the upper portion of the retina. In the past support for either the upper or lower portion of the retina was possible and there was no manner for simultaneous support of both the upper and lower portion of the retina. Another beneficial effect is that the combination of perfluorocarbon liquid and silicone prevents the emulsification of perfluorocarbon liquid and allows the combination to left in the eye for longer periods of time. The combination of perfluorocarbon and silicone has been left in the eye for over eight weeks without any signs of emulsification of the perfluorocarbon liquid. Another beneficial effect is that the combination of perfluorocarbon liquid and silicone is non-toxic.

There has been shown and described a novel combination of perfluorocarbon liquids and silicone and a method of using the combination which fulfills all of the objects and advantages sought therefor. It will be apparent to those skilled in the art, however, that many changes, modifications, variations, and other uses and applications of the subject combination are possible and contemplated. All such changes, modifications, variations, and other uses and applications which do not depart from the spirit and scope of this invention are deemed to be covered by the invention, which is limited only by the claims which follow.

What is claimed is:

1. A combination for use in the treatment of a retinal detachment of an eye comprising an amount of perfluorocarbon liquid and an amount of silicone which are injected into the eye in amounts effective to treat the retinal detachment, and the amount of silicone having a viscosity within the range of 10 centistokes and 1,000 centistokes.

2. The combination of claim 1 wherein the amount of perfluorocarbon liquid is equal to the amount of silicone.

3. The combination of claim 1 wherein the amount of perfluorocarbon liquid is twice that of the amount of silicone.

4. The combination of claim 1 wherein the amount of silicone is twice that of the amount of perfluorocarbon liquid.

5. The combination of claim 1 wherein a preferred range of the viscosity of silicone is between 250 centistokes and 1,000 centistokes.

6. The combination of claim 1 wherein the amount of perfluorocarbon liquid is perfluorophenanthrene.

7. The combination of claim 1 wherein the amount of perfluorocarbon liquid is perfluorooctylbromide.

8. The combination of claim 1 wherein the perfluorocarbon liquid supports the lower portion of the retina and the silicone supports the upper portion of the retina.

9. A method of treating a retinal detachment of an eye comprising introducing into the eye an amount of perfluorocarbon liquid and an amount of silicone which are in amounts effective to treat the retinal detachment, and the amount of silicone having a viscosity within the range of 10 centistokes and 1,000 centistokes.

10. The method of claim 9 wherein the amount of perfluorocarbon liquid is equal to the amount of silicone.

11. The method of claim 9 wherein the amount of perfluorocarbon is twice the amount of silicone.

12. The method of claim 9 wherein the amount of silicone is twice the amount of perfluorocarbon liquid.

13. The method of claim 9 wherein the preferred range of the viscosity of the amount of silicone is between 250 centistokes and 1,000 centistokes.

14. The method of claim 9 wherein the amount of perfluorocarbon liquid and the amount of silicone are introduced into the vitreous of the eye.

15. The method of claim 14 wherein the vitreous is substantially replaced with the combination of perfluorocarbon liquid and silicone.

16. The method of claim 9 wherein the perfluorocarbon liquid is perfluorophenanthrene.

17. The method of claim 9 wherein the perfluorocarbon liquid is perfluorooctylbromide.

18. The method of claim 9 wherein the perfluorocarbon liquid supports the lower portion of the retina and the silicone supports the upper portion of the retina.

19. The method of claim 9 wherein the combination is injected into the vitreous of the eye.

20. The method of claim 19 wherein the vitreous is replaced substantially with the combination.

* * * * *